(12) United States Patent
Foley

(10) Patent No.: US 9,066,973 B2
(45) Date of Patent: Jun. 30, 2015

(54) WEIGHT LOSS COMPOSITION AND METHOD

(75) Inventor: Ryan Jason Foley, Toronto (CA)

(73) Assignee: NUVOCARE HEALTH SCIENCES INC., Toronto, Ontario (CA)

(*) Notice: Subject to any disclaimer, the term of this patent is extended or adjusted under 35 U.S.C. 154(b) by 667 days.

(21) Appl. No.: 12/874,673

(22) Filed: Sep. 2, 2010

(65) Prior Publication Data

US 2011/0052754 A1 Mar. 3, 2011

Related U.S. Application Data

(60) Provisional application No. 61/239,380, filed on Sep. 2, 2009.

(51) Int. Cl.

| | |
|---|---|
| *A61K 36/00* | (2006.01) |
| *A61K 36/63* | (2006.01) |
| *A61K 36/81* | (2006.01) |
| *A23L 1/30* | (2006.01) |
| *A23L 1/304* | (2006.01) |

(52) U.S. Cl.
CPC ............... *A61K 36/81* (2013.01); *A61K 36/63* (2013.01); *A23L 1/3002* (2013.01); *A23L 1/304* (2013.01)

(58) Field of Classification Search
None
See application file for complete search history.

(56) References Cited

U.S. PATENT DOCUMENTS

| | | | | |
|---|---|---|---|---|
| 2005/0025844 | A1* | 2/2005 | Boldt | 424/734 |
| 2005/0136138 | A1* | 6/2005 | Pushpangadan et al. | 424/756 |
| 2005/0260285 | A1* | 11/2005 | DiMateeo-Leggio | 424/725 |
| 2005/0288360 | A1* | 12/2005 | Raederstorff et al. | 514/456 |
| 2006/0240125 | A1* | 10/2006 | Astrup et al. | 424/682 |
| 2006/0246196 | A1* | 11/2006 | Lawson | 426/548 |
| 2006/0251750 | A1* | 11/2006 | Tabor | 424/757 |
| 2007/0020738 | A1* | 1/2007 | Amino et al. | 435/134 |
| 2007/0116779 | A1* | 5/2007 | Mazzio | 424/539 |
| 2010/0222422 | A1* | 9/2010 | Romero et al. | 514/456 |

OTHER PUBLICATIONS

Ramawat et al, Guggulsterone: a potent natural hypolipidemic agent from *Commiphora wightii*—Problems, perseverance, and prospects. Ramawat, KG [Editor]; Merillon, JM [Editor]. (2008) pp. 101-121. Bioactive Molecules and Medicinal Plants. Publisher: Springer-Verlag Berlin, Heidelberger Platz 3, D-14197 Berlin, Germany.*
Hiroshi et al, Inhibitory effect of green coffee bean extract on fat accumulation and body weight gain in mice. BMC complementary and alternative medicine, (2006) vol. 6, pp. 9. Electronic Publication: Mar. 17, 2006. Journal code: 101088661. E-ISSN: 1472-6882. L-ISSN: 1472-6882.*
Ramawat et al, A preliminary anithyperglycemic and antinociceptive activity evaluation of *Amorphophallus campanulatus* corms. International Journal of Pharmacy and Pharmaceutical Sciences, (2014) vol. 6, No. Suppl. 2, pp. 613-616.*
Beattie, Ginger phytochemicals mitigate the obesogenic effects of a high-fat diet in mice: a proteomic and biomarker network analysis. Molecular nutrition & food research, (Sep. 2011) vol. 55 Suppl 2, pp. S203-S2013.*
Abdo et al, Biological activities of *Allium sativum*. Japj.Pharmacol., (1969) vol. 19, No. 1, pp. 1-4.*
de Sales et al, .alpha.-amylase inhibitors: A review of raw material and isolated compounds from plant source. Journal of Pharmacy and Pharmaceutical Sciences, (Jan. 25, 2012) vol. 15, No. 1, pp. 141-183.*

* cited by examiner

*Primary Examiner* — Qiuwen Mi

(74) *Attorney, Agent, or Firm* — TraskBritt, P.C.

(57) ABSTRACT

A composition is provided for promoting weight loss. This comprises a component for supporting healthy thyroid function; a component for increasing satiety; a component for inhibiting carbohydrate uptake and usage; a component for increasing calorie expenditure; and a component for increasing fatty acid oxidation therefore improving lean body composition. A method promoting weight loss in a human is also provided. The method comprises the following steps: supporting healthy thyroid function; increasing satiety; inhibiting carbohydrate uptake and usage; increasing calorie expenditure; and increasing fatty acid oxidation therefore improving lean body composition.

1 Claim, 1 Drawing Sheet

WEIGHT LOSS METHODS & COMPOSITION SELECTION CHART

| STEP #1 Support healthy thyroid Function | | | STEP #2 Increase Satiety | | | STEP #3 Inhibit Carbohydrate Uptake & Usage | | | STEP #4 Increase Calorie Expenditure | | | STEP #5 Increase Fatty Acid Release & Oxidation | | |
|---|---|---|---|---|---|---|---|---|---|---|---|---|---|---|
| Ingredient | min/day | max/day | Ingredient | min/day | max/day | Ingredient | min/day | max/day | Ingredient | min/day | max/day | Ingredient | min/day | max/day |
| Iodine (as Potassium Iodide) | 0.1mg | 1mg | Capsicum Extract (Capsicum annum L) [0.5-98% Total Capsaicinoids including Capsaicin, Dihydro Capsaicin, and Nor Dihydro Capsaicin] | 5mg | 250mg | Chromium (as Chromium Polynicotinate) | 0.9mg | 5mg | Green Tea Extract (Camellia sinensis) (leaf)[Standardized to 98% Polyphenols, 75-80% Catechins, 45%-60% EGCg] | 200mg | 1000mg | 99% Raspberry Ketones (aromatic compound of Red Raspberry) | 5mg | 1000mg |
| Selenium (as L-selenomethionine) | 5mg | 25mg | Brazilian Cha De Bugre Extract (Cordia salicifolia)[10:1] | 5mg | 500mg | Green Coffee Extract (Coffea arabica) (Bean)[50% Chlorogenic Acid, 10% 5-Caffeoylquinic acid, 50% Polyphenols] | 100mg | 1000mg | B-Phenylethylamine HCL | 1mg | 1000mg | Coleus Forskohlii (root) [Standardized to 10-98% forskolin] | 5mg | 500mg |
| Olive (olea europaea) Leaf Extract [Standardized for 10% 12% Oleuropein] | 50mg | 500mg | Hoodia gordonii Cactus plant extract | 1mg | 3000mg | White Kidney Bean Extract (Phaseolus Vulgaris) | 1mg | 4500mg | Ginger root (Zingiber officinalis) [Standaridized to 5-99% Gingerols] | 1mg | 3000mg | brown seaweed (Undaria pinnatifida) extract [standardized to 1-20% fucoxanthin] | 1mg | 300mg |
| Guggulsterones (Derived from Guggul Tree Resin) | 5mg | 50mg | Korean Pine Nut (Pinus koralensis) [containing pinolenic acid] | 1mg | 9000mg | Bauhinia megalandra aqueous leaf extract | 1mg | 1500mg | Quebracho tree extract | 1mg | 500mg | L-Carnitine | 1mg | 1500mg |
| Bladderwrack (Fucus vesiculosis) | 5mg | 2000mg | jojoba meal (Simmondsia chinensis) Extract [standardized to 1-99% Simmondsin] | 1mg | 1500mg | Mulberry Powdered Extract (Morus alba) (leaf) [Standardized to 2-10%] | 1mg | 1500mg | 1,3 Dimethylamylamine | 1mg | 50mg | Clary Sage Extract [Standardized to 50-98% Sclareolide] | 1mg | 200mg |
| Kelp | 5mg | 2000mg | red kidney bean extract [Standardized for 1-99% phytohemagglutinin] | 1mg | 7500mg | gymnema sylvestre [Standardized to 25-75% Gymnemic Acid] | 1mg | 1000mg | Grapefruit extract [Standardized to 99% Naringin] | 1mg | 100mg | Quercetin | 1mg | 1500mg |
| L-Tyrosine | 1mg | 3000mg | Griffonia simplicifolia bean extract [20-99% 5-Hydroxytryptophan] | 1mg | 4500mg | | | | | | | | | |

WEIGHT LOSS COMPOSITION AND METHOD

This application is related to and claims priority to U.S. Provisional Application No. 61/239,380 filed on Sep. 2, 2009.

FIELD OF THE INVENTION

The present invention relates to a method, process and composition for the treatment of obesity and aiding in weight loss. In particular, the invention relates to a method and composition for improving the core physiological weight loss mechanisms that take place in the body to deliver effective weight loss.

BACKGROUND OF THE INVENTION

With the increased levels of obesity present in society and the relatively recent focus on maintaining a healthy weight, a number of dietary supplements and other weight loss compositions have been produced. A number of these rely heavily on methylxanthines, such as caffeine, and often potential dangerous levels of such. Caffeine-based weight loss products have a number of side effects, including adrenal burnout, increased blood pressure, mood swings, jitteriness and anxiety. Such side effects are undesirable and potentially hazardous to the health. Other weight loss products often include a large amount of fibre or fibre compounds which increase potential allergic reactions and may result in bloating and/or gas.

There is therefore a need for a weight loss method and composition that stimulates the physiological mechanisms relating to weight loss to provide at least one of optimized, safe, and effective weight loss. There is a further need for a weight loss composition that uses ingredients which have been shown to be safe for consumption in humans

SUMMARY OF THE INVENTION

In accordance with the present invention there is provided a composition, method and process for supporting weight loss.

The composition of the present invention includes at least one of a component for supporting healthy thyroid function; a component for increasing satiety; a component for inhibiting carbohydrate uptake and usage; a component for increasing calorie expenditure; and a component for increasing fatty acid oxidation.

Preferably, the composition of the present invention includes any three of a component for supporting healthy thyroid function; a component for increasing satiety; a component for inhibiting carbohydrate uptake and usage; a component for increasing calorie expenditure; and a component for increasing fatty acid oxidation.

Most preferably, the composition of the present invention includes a component for supporting healthy thyroid function; a component for increasing satiety; a component for inhibiting carbohydrate uptake and usage; a component for increasing calorie expenditure; and a component for increasing fatty acid oxidation.

The present invention also provides a method for promoting weight loss in a human comprising at least one of the steps of: supporting healthy thyroid function; increasing satiety; inhibiting carbohydrate uptake and usage; increasing calorie expenditure; and increasing fatty acid oxidation.

Preferably, the method comprises at least three of the steps of: supporting healthy thyroid function; increasing satiety; inhibiting carbohydrate uptake and usage; increasing calorie expenditure; and increasing fatty acid oxidation.

Most preferably, the method comprises the steps of: supporting healthy thyroid function; increasing satiety; inhibiting carbohydrate uptake and usage; increasing calorie expenditure; and increasing fatty acid oxidation.

According to one aspect of the present invention, there is provided a composition for promoting weight loss comprising at least three of: a component for supporting healthy thyroid function; a component for increasing satiety; a component for inhibiting carbohydrate uptake and usage; a component for increasing calorie expenditure; and a component for increasing fatty acid oxidation.

According to another aspect of the present invention, there is provided a composition for promoting weight loss comprising: a component for supporting healthy thyroid function; a component for increasing satiety; a component for inhibiting carbohydrate uptake and usage; a component for increasing calorie expenditure; and a component for increasing fatty acid oxidation.

According to another aspect of the present invention, there is provided a method promoting weight loss in a human comprising the following steps: supporting healthy thyroid function; increasing satiety; inhibiting carbohydrate uptake and usage; increasing calorie expenditure; and increasing fatty acid oxidation.

BRIEF DESCRIPTION OF THE DRAWINGS

The novel features which are believed to be characteristic of the present invention, as to its structure, organization, use and method of operation, together with further objectives and advantages thereof, will be better understood from the following drawing in which a presently preferred embodiment of the invention will now be illustrated by way of example. It is expressly understood, however, that the drawing is for the purpose of illustration and description only, and is not intended as a definition of the limits of the invention. In the accompanying drawing:

FIG. 1 is a chart that sets out preferred components of the composition of the present invention.

DETAILED DESCRIPTION

The present invention includes a method for supporting weight loss that comprises up to five steps. These steps include (1) supporting healthy thyroid function; (2), increasing satiety; (3) inhibiting carbohydrate uptake and usage; (4) increasing caloric expenditure; and (5) increasing fatty acid oxidation and therefore improving lean body composition. The method can be carried out by implementing any one of these steps. Preferably, at least three of the steps are carried out. Most preferably, all five steps are carried out.

The present invention also includes a composition for supporting weight loss. The composition includes a component for carrying out each step or steps required for supporting weight loss. These components may include (1) a component for supporting healthy thyroid function; (2) a component for increasing satiety; (3) a component for inhibiting carbohydrate uptake and usage; (4) a component for increasing caloric expenditure; and (5) a component for increasing fatty acid oxidation therefore improving lean body composition. The composition can include any one of these components. Preferably, the composition includes three of the above components. Most preferably, the composition includes all five of the above components.

According to step (1), supporting healthy thyroid function is preferably accomplished by supporting the production of adequate thyroid hormones. Without adequate thyroid function, body metabolism will slow and an optimized weight loss state will not be created in the body.

According to step (2), increasing satiety supports the consumption of less food (calorie) intake helping to encourage a caloric deficit state in the body. This ultimately helps force the body to target fat storage and to release fat reserves to be used as energy.

According to step (3), inhibiting carbohydrate uptake and usage preferably occurs by inhibiting carbohydrate absorption in the small intestine and/or limiting the release of glucose into the blood stream from the liver, thus causing the body to target fat stores and release fat reserves to be used as energy.

According to step (4), caloric expenditure is increased. Increasing caloric expenditure encourages a caloric deficit state helping to stimulate the body to release stored fatty acids from adipose tissue.

According to step (5), fatty acid oxidation is increased. The oxidation of fatty acids is the mechanism by which the mitochondria of the cell breaks down released fatty acids resulting in the production of heat and energy. By increasing fatty acid oxidation, the elimination of stored body fat can be optimized, leading to less fat stores and an improvement in lean body composition.

The component for supporting healthy thyroid function is preferably any one of iodine, selenium, olive leaf and/or pulp extract and guggul tree resin.

Preferably, the guggul tree resin is provided under the GuggulEZ100™ brand, and is preferably standardized for 95% E and Z guggulsterones isomers. It supports healthy thyroid function and resting metabolism by supporting the production of thyroxine and the conversion of thyroxine to thriodothyronine. Preferably, each unit of the composition includes from 5 mg to 50 mg of guggulsterones. The recommended daily dose of guggulsterones for the purposes of the present invention is from 5 mg to 50 mg.

Iodine is preferably provided as potassium iodide. The inclusion of iodine supports healthy thyroid function and resting metabolism for the purpose of healthy weight loss. Preferably, each unit of the composition includes from 0.1 mg to 1 mg of potassium iodide. This provides from 0.076 mg to 0.76 mg of elemental iodine per unit of the composition. The recommended daily dose of iodine for the purposes of the present invention is from 0.1 mg to 1 mg of potassium iodide or from 0.076 mg to 0.76 mg of elemental iodine. The most preferred amount of potassium iodide is 0.149 mg per unit of the composition which provides 0.11 mg of elemental iodine per unit. The preferred daily dose of potassium iodide is 0.3 mg which provides 0.228 mg of elemental iodine.

Selenium is preferably provided as L-selenomethionine. Selenium supports healthy thyroid function by aiding in the production of thyroid hormones for the purposes of healthy weight loss. Preferably, each unit of the composition includes from 5 mg to 25 mg of L-selenomethionine which provides 0.025 mg to 0.125 mg of elemental selenium. The recommended daily dose of L-selenomethionine for the purposes of the present invention is from 5 mg to 25 mg. Preferably, each unit of the composition includes 8.25 mg of L-selenomethionine which provides 0.04125 mg of elemental selenium. The preferred daily dose of L-selenomethionine is 16.5 mg which provides 0.0825 mg of elemental selenium.

The olive leaf and/or pulp extract supports healthy thyroid function and resting metabolism. It is preferably standardized for 10%-20% oleuropein and/or a percentage greater than 1-10% hytroxytyrosol. Preferably, each unit of the composition includes from 50 mg to 500 mg of olive leaf extract. The recommended daily dose of olive leaf extract for the purposes of the present invention is from 50 mg to 500 mg.

Bladderwack (*Fucus viesiculosis*) kelp and L-Tyrosine may also be included as a component for supporting healthy thyroid function. The amounts of Bladderwack (*Fucus viesiculosis*), kelp and L-Tyrosine are set out in FIG. 1. Preferably, the component for supporting healthy thyroid function is present in an amount of from about 0.01% to about 70% percent by weight of the composition.

The component for increasing satiety is preferably a capsicum extract. The capsicum extract, such as available under the Capsimax® brand, is a composition of 2% total capsaicinoids including capsaicin, dihydro capsaicin and nor dihydro capsaicin. It is capable of delivering a minimum of 300,000 Scoville Heat Units (SHU). The capsicum extract is provided to increase satiety causing less food consumption. It increases caloric expenditure aiding in weight loss. Preferably, each unit of the composition includes from 5 mg to 250 mg of capsicum extract. The recommended daily dose of capsicum extract for the purposes of the present invention is from 5 mg to 250 mg.

Other components for increasing satiety include Brazilian Cha De Bugre Extract (*Cordia salcifolia*) [10:1], *Hoodia gordonii* Cactus plant extract, Korean Pine Nut (*Pinus koralensis*) [containing pinolenic acid], jojoba meal (*Simmondsia chinensis*) Extract [standardized to 1-99% Simmondsin], red kidney bean extract [Standardized for 1-99% phytohemagglutinin], and *Griffonia simplicifolia* bean extract [20-99% 5-Hydroxytryptophan]. The amounts are set out in FIG. 1.

The component for increasing satiety function is preferably present in an amount of from about 0.001% to about 70% percent by weight of the composition.

The component for inhibiting carbohydrate uptake and usage is preferably chromium and/or green coffee bean extract. The chromium is preferably provided as chromium polynicotinate, such as available under the ChromeMate® brand. Chromium aids in increasing muscle insulin sensitivity and reduces blood glucose levels. Preferably, each unit of the composition includes from 1 mg to 10 mg of chromium polynicotinate which provides 0.1 mg to 1 mg of elemental chromium. The recommended daily dose of chromium polynicotinate for the purposes of the present invention is from 1 mg to 10 mg. Most preferably, each unit of the composition comprises about 2.6 mg of chromium polynicotinate which provides 0.26 mg of elemental chromium.

The green coffee bean extract, such as available under the SVETOL® brand, inhibits carbohydrates usage and uptake reducing plasma glucose and forcing the body to tap into fat storage for energy, thus improving lean body composition. Preferably, the green coffee bean extract is standardized to 50% chlorogenic acid with a specific ratio between 5-caffeolyquinic acid and others caffeolyquinic isomers and 65% polyphenols. As an added benefit, the chlogenic acid also increases plasma anti-oxidant levels. Preferably, each unit of the composition includes from 100 mg to 1000 mg of green coffee bean extract. The recommended daily dose of green coffee bean extract for the purposes of the present invention is from 100 mg to 1000 mg.

Other components for inhibiting carbohydrate uptake and usage include white kidney bean extract (*Phaseolus Vulgaris*), *Bauhinia megalandra* aqueous leaf extract, mulberry powder extract and *gymnema sylvestre* Standardized to 25-75% Gymnemic Acid). The amounts are set out in FIG. 1.

Preferably, the component for inhibiting carbohydrate uptake and usage is present in an amount of from about 0.01% to about 70% percent by weight of the composition.

The component for increasing calorie expenditure is preferably green tea extract. The green tea extract, also known as *camellia sinensis*, increases caloric expenditure and fatty acid oxidation. Preferably, the green tea extract is standardized to 98% polyphenols, 80% catechins, and 45% EGCG. As an added benefit, the green tea extract also increases plasma anti-oxidant levels. Preferably, each unit of the composition includes from 200 mg to 1000 mg of green tea extract. The recommended daily dose of green tea extract for the purposes of the present invention is from 200 mg to 1000 mg.

Other components for increasing calorie expenditure within the scope of the present invention include B-Phenyl-ethylamine HCL, ginger root (*Zingiber Officinalis*) [Standardized to 5-99% Gingerols], Quebracho tree extract, 1,3 Dimethylamylamine, Grapefruit extract [Standardized to 99% Naringin]. The amounts are set out in FIG. 1.

Preferably, the component for increasing calorie expenditure is present in an amount of from about 0.001% to about 70% percent by weight of the composition.

The component for increasing fatty acid oxidation is preferably a raspberry ketone and/or green tea extract. A raspberry ketone is an aromatic compound derived from red raspberries. An example of a raspberry ketone is available under the Razberi-K® brand. It supports norepinephrine induced lipolysis and fatty acid oxidization aiding in a healthy weight loss process. Preferably, each unit of the composition includes from 5 mg to 1000 mg of raspberry ketone. The recommended daily dose of raspberry ketone for the purposes of the present invention is from 5 mg to 1000 mg.

Another component for increasing fatty acid oxidation that is within the scope of the present invention is the root of Coleus Forskohli. Preferably, the root of Coleus Forskohli is standardized to 10-98% forskolin. Brown seaweed (Undaria pinnatifida) extract may also be used as the component for increasing fatty acid oxidation. Preferably, it is standardized to 1-20% fucoxanthin. Other acceptable components for increasing fatty acid oxidation that are within the scope of the present invention include L-Carnitine, Quercetin and Clary Sage Extract. Preferably, the Clary Sage Extract is standardized to 50-98% Sclareolide. The amounts are set out in FIG. 1.

Preferably, the component for increasing fatty acid oxidation is present in an amount of from about 0.001% to about 70% percent by weight of the composition.

Preferably, each unit of the composition is formulated in the form of a pill. Each unit of the composition may also be delivered in the form of a gelatin capsule and may further include microcrystalline cellulose, magnesium stearate and silica acting as encapsulation and flow agents.

Preferably, there is provided between approximately 160-240 mg/pill or capsule green coffee bean extract, 240-360 mg/pill or capsule green tea extract, 40-60 mg/pill or capsule capsicum extract, 40-60 mg/pill or capsule raspberry ketones, 40-60 mg/pill or capsule olive leaf extract and 4-6 mg/pill or capsule guggulsterones. Preferably, two pills or capsules per day should be consumed for optimal results.

A preferred formulation for the composition includes 50 mg per unit (preferably a pill/unit or capsule) of olive leaf (*olea europaea*) extract which is standardized for 10% to 12% Oleuropein; 5 mg per unit of GuggulEZ100™ 95% E & Z Guggulsterones (derived form guggul tree resin); 8.25 mg per unit of SeleniumSeLECT® brand L-selenomethionine, 50 mg per unit of Capsimax® capsicum extract; 200 mg per unit of SVETOL® brand green coffee bean extract; 2.6 mg per unit of ChromeMate® brand chromium polynicotinate; 300 mg per unit of green tea extract; and 50 mg per unit of Razberi-K® brand raspberry ketones. The total weight of the unit is about 552.6 mg. It will be understood that this formulation is for example only and variations are permitted without deviating from the scope of the present invention.

Preferably, the composition will be administered in a pill or capsule twice daily, prior to a person's two largest meals, for a minimum of 60 days. Alternative dosages will be known to those skilled in the art.

Alternatives include administering the composition in other forms including a powder, liquid, 2-piece encapsulation, various pills with carriers and binders, effervescent drinks in powder and liquid form, chewing gums, time-released capsules and caplets, rapid-release capsules and caplets, nanoparticulation of the ingredients, energy shot format, Two-Piece liquid capsules, i.e. LiCaps®, and soft-gel liquid capsules.

EXAMPLES

Example 1

A female subject took one capsule of the preferred formulation twice daily with her two largest meals (breakfast and dinner) for a 50-day test period. The preferred formulation includes 50 mg per capsule of olive leaf (*olea europaea*) extract which is standardized for 10% to 12% Oleuropein; 5 mg per capsule of GuggulEZ100™ 95% E & Z Guggulsterones (derived form guggul tree resin); 0.15 mg per capsule of potassium iodide; 8.25 mg per capsule of SeleniumSeLECT® brand L-selenomethionine; 50 mg per capsule of Capsimax® brand capsicum extract; 200 mg of SVETOL® brand green coffee bean extract; 2.6 mg per capsule of ChromeMate®vbrand chromium polynicotinate; 300 mg per capsule of green tea extract; and 50 mg per capsule of Razberi-K® brand raspberry ketones. The subject achieved weight loss of 16 pounds, a 3.0 inch reduction in waist circumference and a 2.5 inch reduction in hip circumference.

Example 2

A female subject took one capsule of the preferred formulation twice daily with her two largest meals (breakfast and dinner) for a 50-day test period. The preferred formulation includes 50 mg per capsule of olive leaf (*olea europaea*) extract which is standardized for 10% to 12% Oleuropein; 5 mg per capsule of GuggulEZ100™ 95% E & Z Guggulsterones (derived form guggul tree resin); 0.15 mg per capsule of potassium iodide; 8.25 mg per capsule of SeleniumSeLECT® brand L-selenomethionine; 50 mg per capsule of Capsimax® brand capsicum extract; 200 mg of SVETOL® brand green coffee bean extract; 2.6 mg per capsule of ChromeMate® brand chromium polynicotinate; 300 mg per capsule of green tea extract; and 50 mg per capsule of Razberi-K® brand raspberry ketones. The subject achieved weight loss of 17 pounds, and a 4.5 inch reduction in waist circumference.

Example 3

A female subject took one capsule of the preferred formulation twice daily with her two largest meals (breakfast and dinner) for a 50-day test period. The preferred formulation includes 50 mg per capsule of olive leaf (olea europaea) extract which is standardized for 10% to 12% Oleuropein; 5 mg per capsule of GuggulEZ100™ 95% E & Z Guggulsterones (derived form guggul tree resin); 0.15 mg per capsule of potassium iodide; 8.25 mg per capsule of SeleniumSe-LECT® brand L-selenomethionine; 50 mg per capsule of Capsimax® brand capsicum extract; 200 mg of SVETOL® brand green coffee bean extract; 2.6 mg per capsule of ChromeMate® brand chromium polynicotinate; 300 mg per capsule of green tea extract; and 50 mg per capsule of Razberi-K® brand raspberry ketones. The subject achieved weight loss of 11 pounds, a 4.0 inch reduction in waist circumference and a 2.0 inch reduction in hip circumference.

While the aforementioned method and composition have been described with regard to specific examples, it will be understood by those skilled in the art that variations and common substitutions may be applied without deviating from the scope of the present invention.

What is claimed is:

1. A composition for promoting weight loss consisting of:
50 mg olive leaf extract,
5 mg 95% E & Z guggulsterones,
0.15 mg potassium iodide,
8.25 mg L-selenomethionine,
50 mg capsicum,
200 mg green coffee bean extract,
2.6 mg chromium polynicotinate,
300 mg green tea extract and
50 mg raspberry ketone.

* * * * *